US007420679B2

(12) United States Patent
Treado et al.

(10) Patent No.: US 7,420,679 B2
(45) Date of Patent: Sep. 2, 2008

(54) METHOD AND APPARATUS FOR EXTENDED HYPERSPECTRAL IMAGING

(75) Inventors: Patrick J. Treado, Pittsburg, PA (US); Charles W. Gardner, Jr., Gibsonia, PA (US); Matthew P. Nelson, Harrison City, PA (US)

(73) Assignee: ChemImage Corporation, Pittsburgh, PA (US)

( * ) Notice: Subject to any disclaimer, the term of this patent is extended or adjusted under 35 U.S.C. 154(b) by 192 days.

(21) Appl. No.: 11/229,539

(22) Filed: Sep. 20, 2005

(65) Prior Publication Data

US 2006/0050278 A1 Mar. 9, 2006

Related U.S. Application Data

(63) Continuation of application No. 11/016,847, filed on Dec. 21, 2004, now abandoned.

(60) Provisional application No. 60/583,842, filed on Jun. 30, 2004.

(51) Int. Cl.
  *G01J 3/51* (2006.01)
  *G01N 21/31* (2006.01)

(52) U.S. Cl. ............ 356/419; 356/51; 356/301; 356/417; 250/339.05; 250/372

(58) Field of Classification Search ............ 356/417, 356/301, 303, 317, 320, 326; 600/160, 476; 250/458.1, 461.2, 459.1, 461.1, 462.1, 266; 359/355, 356, 357, 361, 368, 372, 373, 374, 359/385, 388, 389, 363
See application file for complete search history.

(56) References Cited

U.S. PATENT DOCUMENTS

| 6,485,413 | B1 * | 11/2002 | Boppart et al. ............ 600/160 |
| 6,998,614 | B2 * | 2/2006 | Lanoue ................. 250/339.05 |
| 2005/0024640 | A1 * | 2/2005 | Fateley et al. ............ 356/330 |
| 2005/0264813 | A1 * | 12/2005 | Giakos ..................... 356/369 |

OTHER PUBLICATIONS

Exline, D.L., et al., "Forensic Applications of Chemical Imaging: Latent Fingerprint Detection Using Visible Absorption and Luminescence," Journal of Forensic Science, vol. 48, No. 5, Sep. 2003.
Exline, D.L., et al., "Improved Fingerprint Visualization Using Luminescence and Visible Reflectance Chemical Imaging," Forensic Science Communications, vol. 5, No. 3, Jul. 2003.

(Continued)

*Primary Examiner*—F. L. Evans
*Assistant Examiner*—Abdullahi Nur
(74) *Attorney, Agent, or Firm*—Duane Morris LLP (57) ABSTRACT

The disclosure relates to method and apparatus for obtaining a multimodal hyperspectral image of a sample for widefield spectral analysis. An apparatus according to one embodiment may include a plurality of optical lenses configured to interchangeably receive photons and focus the photons; a plurality of tunable filters positioned in a filter housing, each tunable filter selectively receiving the focused dispersed photons from one of the plurality of optical lenses, each tunable filter providing wavelength-selective filtered photons; a first optical camera and a second optical cameras for selectively receiving the wavelength-selective filtered photons from each of the plurality of tunable filters and combining said filtered photons to form a hyperspectral spatially accurate, wavelength-resolved image of the sample.

66 Claims, 8 Drawing Sheets

OTHER PUBLICATIONS

"Forensic Sciences: Review of Status and Needs," Office of Law Enforcement Standards, National Institute of Standards and Technology, Feb. 1999.

Stoilovic, M, et al., "The Application of Light in Forensic Science & A Modern Approach to Fingerprint Detection and Enhancement," AFP Workshop Manual, Forensic Services, Australian Federal Police, Oct. 2000.

* cited by examiner

METHOD AND APPARATUS FOR EXTENDED HYPERSPECTRAL IMAGING

The instant application claims the filing-date benefit of Provisional Application No. 60/583,842 filed Jun. 30, 2004, and is a Continuation of U.S. patent application Ser. No. 11/016,847 filed Dec. 21, 2004, now abandoned the specifications of which are incorporated herein in their entirety.

BACKGROUND

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e. chemical) imaging typically comprise an illumination source, image gathering optics, focal plane array imaging detectors and imaging spectrometers.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscope or rigid borescopes can be employed. For very large scale objects, such as planetary objects, telescopes are appropriate image gathering optics.

For detection of images formed by the various optical systems, two-dimensional, imaging focal plane array (FPA) detectors are typically employed. The choice of FPA detector is governed by the spectroscopic technique employed to characterize the sample of interest. For example, silicon (Si) charge-coupled device (CCD) detectors or CMOS detectors are typically employed with visible wavelength fluorescence and Raman spectroscopic imaging systems, while indium gallium arsenide (InGaAs) FPA detectors are typically employed with near-infrared spectroscopic imaging systems.

Spectroscopic imaging of a sample can be implemented by one of two methods. First, a point-source illumination can be provided on the sample to measure the spectra at each point of the illuminated area. Second, spectra can be collected over the an entire area encompassing the sample simultaneously using an electronically tunable optical imaging filter such as an acousto-optic tunable filter (AOTF) or a liquid crystal tunable filter ("LCTF"). Here, the organic material in such optical filters are actively aligned by applied voltages to produce the desired bandpass and transmission function. The spectra obtained for each pixel of such an image thereby forms a complex data set referred to as a hyperspectral image which contains the intensity values at numerous wavelengths or the wavelength dependence of each pixel element in this image.

The ability to improve discrimination testing of inks, stains, fibers and cloth as well as to improve visualization of fingerprints and thin layer chromatography plates are critical to the forensic analysis. Such testing often requires obtaining the spectrum of a sample at different wavelengths. Conventional spectroscopic devices operate over a limited ranges of wavelength due to the operation ranges of the detectors or tunable filters possible. This enables analysis in the Ultraviolet (UV), visible(VIS), near infrared (NIR), mid infrared (MIR) wavelengths and to some overlapping ranges. These correspond to wavelengths of about 180-380 nm (UV), 380-700 nm(VIS), 700-2500 nm (NIR) and 2500-25000 nm (MIR). Thus, to obtain a comprehensive analysis over a broad range of wavelengths (i.e., a hyperspectral image) more than one spectroscopic device must be applied. Such broad or extended ranges make application time-consuming and not often possible. The sample position and condition may be changed between the first analysis or a later analysis thereby lessening the ability to precisely correlate the spectra obtained at different wavelength ranges. There is a need for rapid, non-invasive instrument capable of operating at IR, NIR, visible, fluorescence, luminescence and Raman modes to provide hyperspectral imaging of the sample.

SUMMARY OF THE DISCLOSURE

In one embodiment, the disclosure relates to a multimodal hyperspectral imaging system for widefield spectral analysis of a sample comprising a first optical lens and a second optical lens configured to interchangeably receive photons scattered by the sample and focus said dispersed photons; a plurality of tunable filters positioned in a filter housing, each tunable filter selectively receiving the focused dispersed photons from one of the first or the second optical lenses, each tunable filter providing wavelength-selective filtered photons; a first optical camera and a second optical cameras for selectively receiving the wavelength-selective filtered photons from each of the plurality of tunable filters and combining said filtered photons to form a hyperspectral spatially accurate, wavelength-resolved image of the sample.

In another embodiment, the disclosure relates to a method for obtaining a hyperspectral image of a sample using an integrated imaging device, the method comprises illuminating the sample with a plurality of photons to produce photons scattered by the sample; providing a first optical lens and a second optical lens for independently collecting the scattered photons and forming focused photons, the first and the second optical lenses providing focused photons having a first and a second wavelength respectively; selectively directing the focused photons to a plurality of optical filters, each of the plurality of optical filters providing filtered photons of the sample; selectively directing each of the plurality of filtered photons to at least one of a first photon detector or a second photon detector, the first and the second photon detectors independently forming a spatially accurate wavelength-resolved image of the sample.

In still another embodiment, the disclosure relates to a system for collecting hyperspectral image of a sample comprising a plurality of optical lenses for receiving photons scattered by the sample and forming focused photons; a filter housing for accommodating a plurality of filters including fixed rejection filters as well as tunable filers, where each tunable filter is adapted to receive focused photons from at least one of the plurality of optical lenses and fixed rejection filter to form a filtered spectrum of the sample; a first and a second optical cameras for receiving the filtered photons from the plurality of tunable filters and forming therefrom a hyperspectral spectrum of the sample; a controller optically connecting one of the plurality of optical lenses with at least one of the plurality of tunable filters. The rejection filters are designed to, among others, reduce the Raleigh scattered laser light for Raman measurements or reduce the fluorescence arising from certain types of samples.

An automated system for collecting hyperspectral image of a sample according to one embodiment of the disclosure can include a processor programmed to (a) illuminate the sample with an illumination source having a first selected wavelength; (b) selectively direct one of a plurality of optical lenses to collect scattered photons from the sample and focus said collected photons; the optical lens adapted to conform to the selected wavelength; (c) direct the focused photons from the optical lens to an optical filter selected from a plurality of optical filters, the selected optical filter conforming to the selected wavelength and receiving the focused collected photons and providing filtered photons; (d) optically transmit the filtered photons from the optical filter to one of a plurality of optical cameras to form an image of the sample in the selected wavelength; repeat steps (a)-(d) for a second selected wavelength to obtain a second image of the sample at the selected wavelength; and combine the images of the sample at the first and the second wavelengths to form a hyperspectral image of the sample.

DETAILED DESCRIPTION

Figure 1:
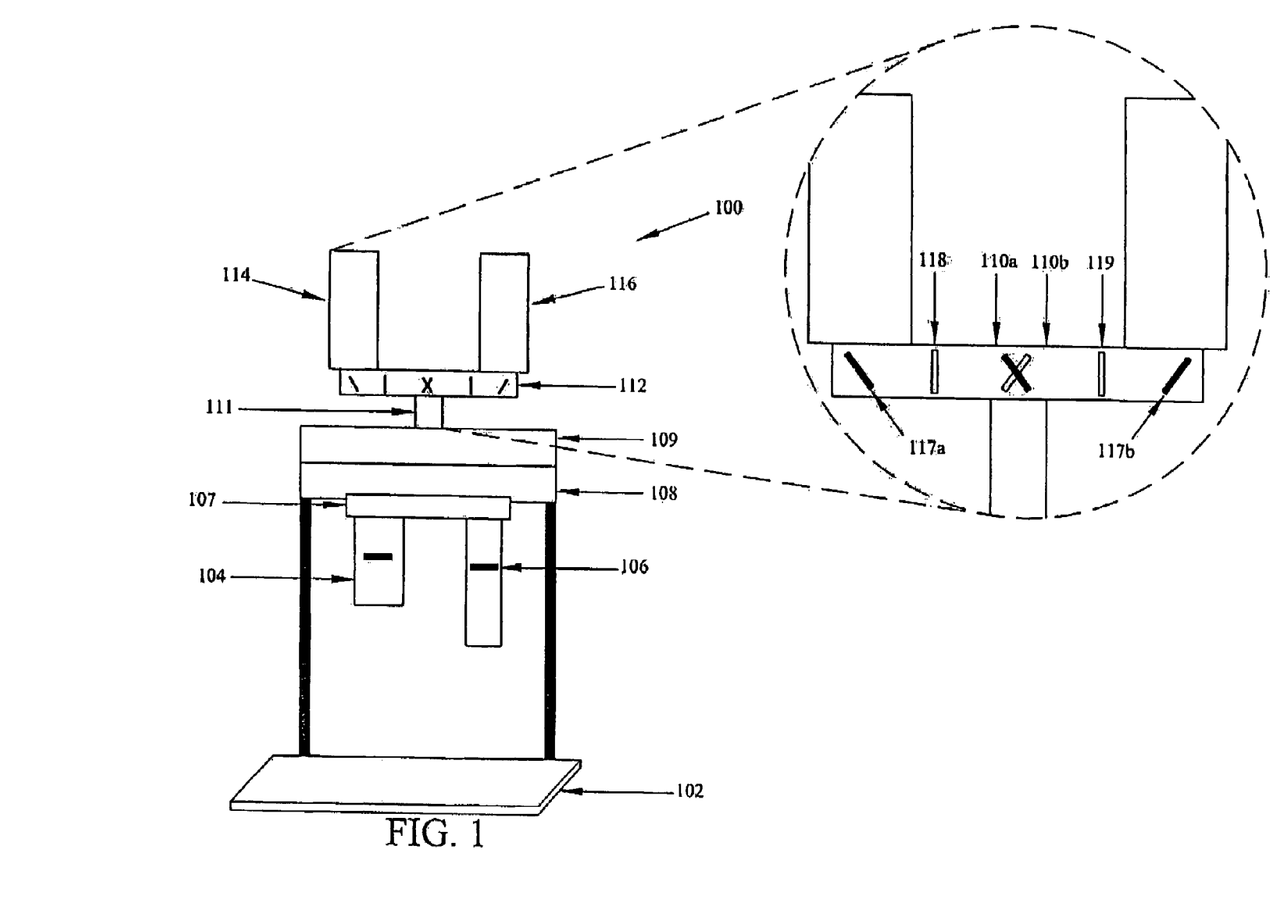
FIG. 1 is a schematic illustration of a multimodal hyperspectral imaging device according one embodiment of the disclosure.

FIG. 1 is a schematic illustration of a multimodal hyperspectral imaging device according one embodiment of the disclosure. The exemplary hyperspectral imaging apparatus 100 shown in FIG. 1, includes base 102 providing a support structure to receive first optical lens 104, second optical lens 106, filter housing 108 and 109. The first or the second optical lens may include a reflective optic. Although not specifically shown, base 102 can be configured to receive and maintain a sample. The first and second optical lenses can be arranged on the structure to interchangeably receive photons and focus said photons to a focal point. The photons include photons reflected, refracted, luminescence, fluorescence, Raman scattered, transmitted, adsorbed or emitted by the sample.

Each of the first and second optical lenses can be selected to have a particular optical specification. The optical specification of the lenses can overlap or can be unique to each lens. The optical lenses can be selected from among VIS, NIR, UV, UV-Vis, zoom lens, low angular field of view, rear aperture, reflective, macro, close-up and micro lenses. The optical lenses may further define an optical train. Moreover, in one embodiment each of the first and second optical lenses can be rigidly mounted on the structure such that each lens can simultaneously and independently receive photons scattered by the sample. Alternatively, the lenses can be mounted on rotating base 107 such that each lens can be positioned to exclusively receive photons scattered by the sample.

Filter housing 108 and 109 can be arranged to receive a plurality of rejection and electronically tunable filters (not shown). The filter housing can be adapted to receive two or more filters depending on the operational range of imaging device 100. In some cases one of filters can be electronically tunable filters and other filters can be holographic or dielectric filters. The filter may also include a rejection filter. In one embodiment, filter housing 108 and 109 can be structured such that scattered photons from each of the first and second optical lens are individually or collectively directed to these filters. In an alternative embodiment, filter housing 108 and 109 can be configured such that scattered photons collected from one or both optical lenses are directed to several filters at one time (either simultaneously or consecutively.) In still another embodiment, the apparatus may include only the filters housing to receive all the filters.

Figure 2A:
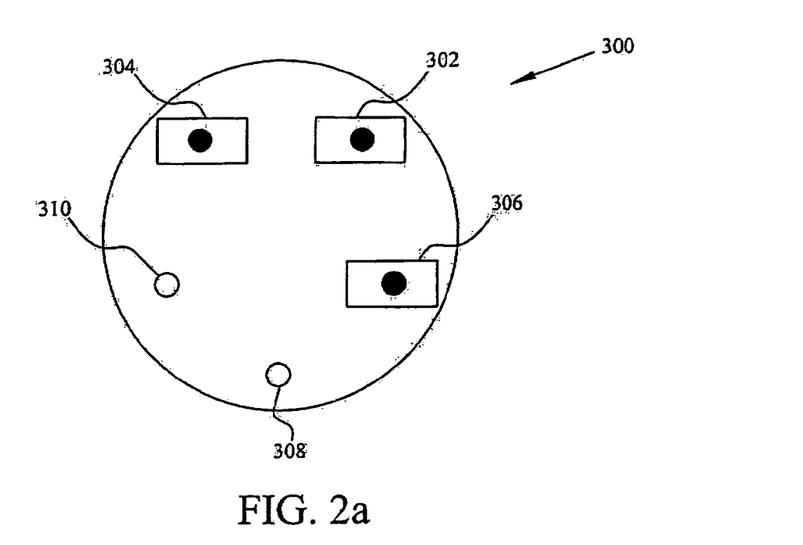
FIGS. 2a and 2b illustrate an exemplary filter housing according to one embodiment of the disclosure.
Figure 2B:
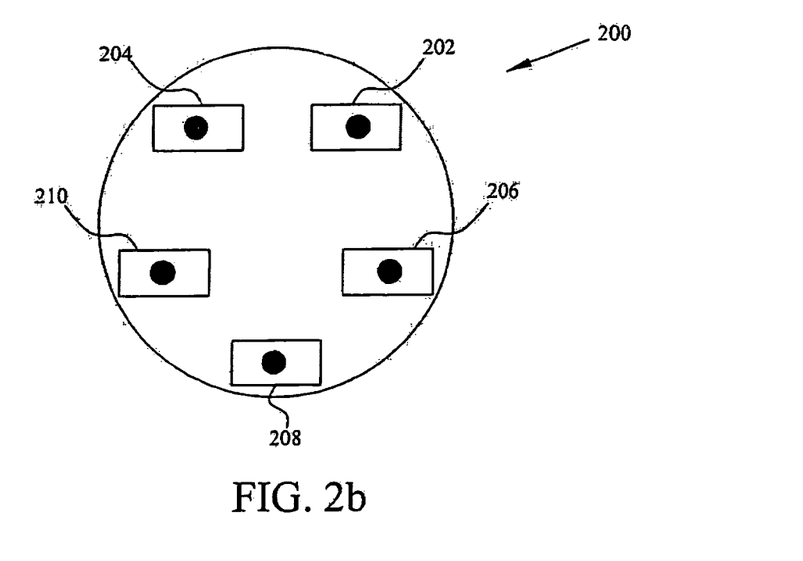

FIG. 2a and 2b illustrate an exemplary filter housing according to one embodiment of the disclosure. Referring to FIG. 2a, filter housing 109 and filters 302, 304 and 306 (as well as slots 308 and 310) are distributed about a central axis. Referring to FIG. 2b filter housing 108 and filters 202, 204, 206, 208 and 210 are distributed about a central axis. Each of the filters 302, 304 and 306 can be fixed rejection filters for special spectral ranges or specific non variable spectral functions, such as but not limited to, fluorescent background filtering. Each of the electronically tunable filters 202, 204, 206, 208 and 210 can be a tunable filter, liquid crystal tunable filter ("LCTF"), acousto-optic tunable filter ("AOTF"), dielectric filter, rotary or linear variable filter, VIS-LCTF (400-700 nm), SW-NIR LCTF (700-1100 nm), MW-NIR LCTF (1100-1700 nm), LW-NIR LCTF (1700-2500 nm) and UV-LCTF (250-400 nm). Each filter of unit 200 can be selected to have unique optical properties and a unique operative range and used in tandem with each or any filters in unit 300. Alternatively, the electronically tunable filters can be selected to have overlapping optical properties. For example, the plurality of filters can be selected to process photons having wavelength in a range of 250-2500 nm. Thus, each filter can operate a segment of the range between 250-2500 nm with possible overlap.

Referring to FIG. 1, the photons are directed to one or more optical detectors or cameras through mirror 110 shown in either of two positions 110a and 110b. Additional mirrors 117a and 117b and focusing lens 118a and 118b are used to respectively deflect and focus the light into the detectors 114 and 116. Mirror 110 can be housed in mirror housing 112 or can be positioned to direct photons from one part of the multimodal hyperspectral device 100 to another part thereof. In the embodiment of FIG. 1, conduit 111 is positioned between filter housing 108 and mirror housing 112. It should be noted that the embodiment of FIG. 1 and conduit 111 are exemplary in nature and that the disclosed principles are not limited to the structure of FIG. 1. Moreover, mirror 112 can be replaced by other means for optically communicating filtered photons from filter housing 108 to the optical detectors or cameras.

The multimodal hyperspectral device 100 is shown to have first camera 114 and second camera 116. Depending on the desired wavelength range, different detectors can be used. For example, UV emission and visible light an be collected on a silicon CCD detector, while NIR-range analysis may use an InGaAs focal plane array ("FPA") detector. Typically, the InGaAs detectors camera are feasible for operation up to 1700 nm. Other FPA detectors can include InSb, MCT, CMOS, CID electron multiplier CCDs and intensified CCDs. Extended range devices can be used for operation up to 2500 nm. Each of first camera 114 and second camera 116 can be a conventional device or maybe tailored for the desired application. To obtain sharp images over the hyperspectral range of 250-2500 nm wavelength, cameras equipped with multiple objective lenses can be used. While the exemplary embodiment of FIG. 1 shows only two detectors or cameras, the principles disclosed herein can be extended to hyperspectral devices having three or more detectors or cameras. Moreover, the detectors or cameras may be coupled to a recording medium for recording the spectrum of the sample.

The apparatus may also include one or more illumination sources adapted to illuminate the sample with photons having wavelength in the desired range. The illumination sources can include, among others, VIS, UV, NIR-IR, IR and Raman photons. The illumination source can be positioned proximate to the hyperspectral imaging device to illuminate the sample from an oblique angle or from below the sample. The illumination sources may be integrated with the hyperspectral imaging device 100 or may be positioned in the proximity of the device. As will be described in greater detail, the illumination sources can be integrated with a control system such that the sample is illuminated by different sources during the analysis.

In an embodiment of the disclosure, the multimodal imaging apparatus can be operated through a controller specifically devised to coordinate the imaging process so as to obtain the desired hyperspectral image. In other words, the controller defines the wavelength of the illumination source and selects the optical device(s) that match the selected wavelength. A controller can be configured to coordinate the appropriate illumination source with the electronically tunable optical filter and the optical detector or camera such that the wavelength of the illumination source would correspond with the wavelength of the optical lens and the operating wavelength of the camera. The controller can comprise a microprocessor programmed to select and exchange the appropriate hardware in combination with electromechanical devices.

Thus, in one embodiment the disclosure relates to an automated system for collecting hyperspectral image of a sample. The automated system can comprise a processor programmed to illuminate the sample with an illumination source having a first selected wavelength. The illumination source maybe one of several possible illumination sources. Next, the processor may selectively direct one of a plurality of optical lenses to collect scattered photons from the sample and focus said collected photons. The processor may select the optical lens in conformance to a pre-defined program or in compliance with a desired wavelength. Thereafter, the processor can direct the focused photons from the optical lens to an optical filter selected from a plurality of optical filters. This step can be accomplished by optically communicating the photons from the lens to the optical filter. As stated, in one embodiment a mirror can be used to implement such communication. As with the selection of the optical lens, one or more optical filters may be selected to conform to a pre-defined program or in compliance with the selected wavelength. Once the appropriate filter(s) have processed the scattered photons the processor may optically transmit the filtered photons from the optical filter to one (or more) of a plurality of optical cameras to form an image of the sample at the selected wavelength. The processor may also display the image or store the image for future display.

Finally, the processor may repeat these steps for a second wavelength range to obtain a second image of the sample at a new wavelength. The images collected at each of the first and second wavelengths can be combined to form a hyperspectral image of the sample. The combination of these distinct images requires not only precise overlay or registration with the target object but a combination that allows the details obtained with the different spectroscopic modes to be complementary and interpretable which is referred to as image fusion.

Image fusion allows the spectroscopic information obtained by two or more spectroscopic methods as described herein can be combined and stored, displayed, or both, as a single data set. By way of example, Raman-scattered light detected from a sample can be amplified (or falsely colored) and displayed together with a visible microscopic image of the sample. In addition, fluorescent light emitted by the sample can be displayed in the same image.

Fusion of spectroscopic information obtained from a single field of view by two or more spectroscopic methods requires mapping of the information obtained by each method to identical or overlapping elements of a data set. By way of example, a visual image can be made by displaying numerous picture elements having a known relationship to one another. For each spectroscopic method for which information is to be represented in the image, the spectroscopic information obtained from a portion of a sample must be mapped to the picture element(s) corresponding to that portion. Information from different spectroscopic methods can be displayed in a picture element corresponding to the same portion of the sample by representing each spectroscopic measurement by an independent variable of light displayed at the picture element. By way of example, a color image based on the Hunter color scale can be generated by, for each picture element of the image: (i) representing brightness assessed by visible light microscopy as luminosity (L) on the Hunter color scale; (ii) representing fluorescent intensity at a selected wavelength assessed by fluorescence spectroscopy as redness (a) on the Hunter color scale; and (iii) representing the intensity of Raman-scattered light at a selected RS value as yellowness (b) on the Hunter color scale. This display methodology is merely an example. Substantially any method of representing independent data sets in a single image or data structure can be used. In one embodiment, the spectroscopic information obtained from a discrete portion of the sample by multiple spectroscopic methods may be mapped to the portion of the sample from which it was obtained, and the method of storing or displaying that information may be preserved so that different spectroscopic properties of the portion can be correlated.

A method for obtaining a hyperspectral image of a sample using an integrated imaging device may include illuminating the sample with photons to produce photons reflected, refracted, luminescence, fluorescence, Raman scattered, transmitted, adsorbed, emitted by the sample. Next, the photons are directed to a first optical lens and a second optical lens. Each optical lens can independently collect the scattered photons and form focused photons. The first and the second optical lenses can provide focused photons of a first and a second wavelength respectively. The first and second wavelengths may be overlapping or distinct from each other. The focused photons are then directed to a plurality of optical filters, each of the plurality of optical filters providing filtered photons of the sample. The filtered photons are selectively directed to one of a plurality of photon detectors to form a spatially accurate, wavelength-resolved image of the sample.

The step of selectively directing the filtered photons to one of a plurality of optical filters can be implemented by a controller programmed to match the photons of a particular wavelength with the appropriate photon detector. In an alternative embodiment, the controller may also selectively match the illumination source with the appropriate optical lens and the appropriate photon detector. The controller can be programmed to select an illumination source having the desired wavelength and optically connect one or more of the optical lenses with one or more of the tunable filters and one or more of the photon detectors. In this manner, the controller integrates various optical lenses, tunable filters and cameras into an integrated computer control system that allows easy transition from one wavelength range to another.

For example, the controller can select a first illumination source having a wavelength of about 250-700 nm. Once the sample has been illuminated, the controller can select one or more of the optical lenses having operating range of about 250-700 nm. Thereafter, the controller can optically communicate photons focused through the optical lens to one or more selective tunable filter. Finally, the controller can arrange for directing the filtered photons from the tunable filter(s) to an appropriate photon detector. Once the sample testing at the first wavelength as been completed, the controller can repeat the operation at a second waveband, for example, a range of about 700-2100 or 700-2500 nm. As a final step, the controller can combine the various images to form a hyperspectral image of the sample.

Figure 3:
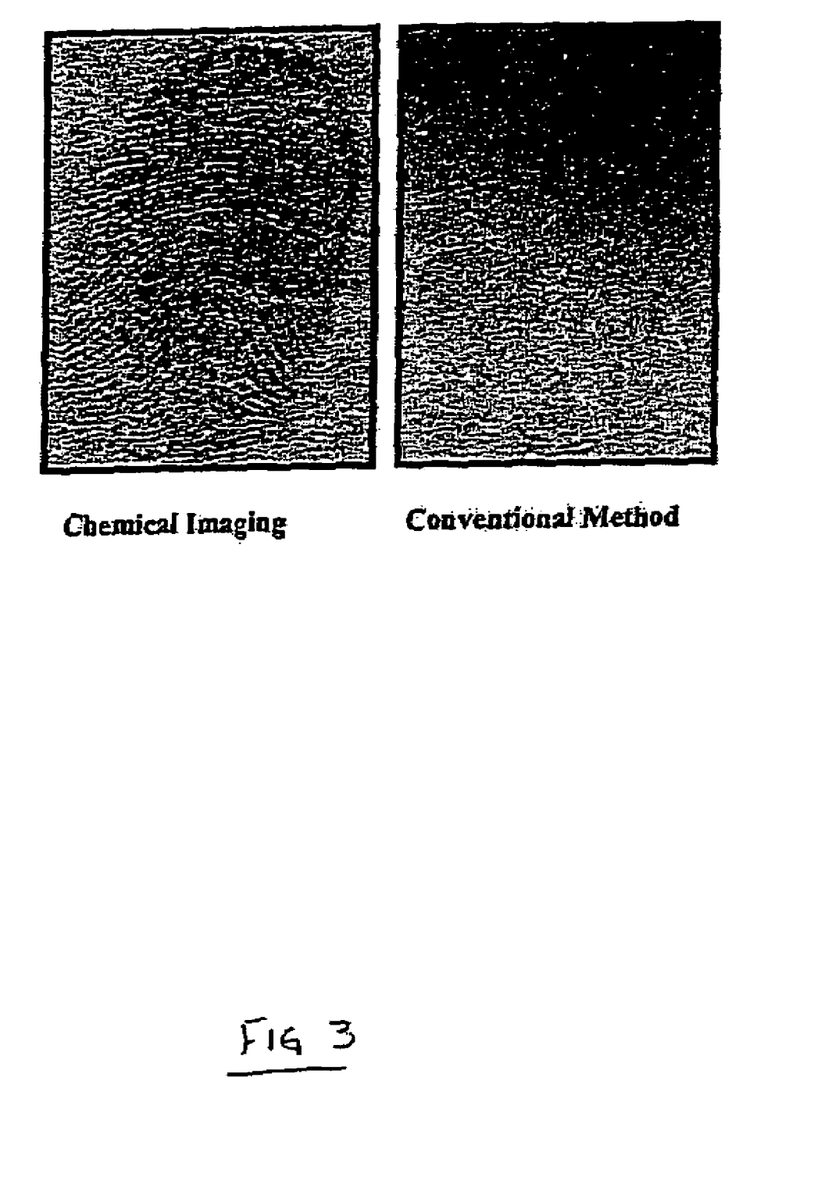
FIG. 3 shows the result of preliminary studies of two-month old latent fingerprints treated with ninhydrin.

The hyperspectral imaging device disclosed herein is particularly advantageous for fingerprint and ink analysis. Conventional fingerprint imaging systems collect data at one specific color (single barrier filter configuration). As a result, fingerprint detection on complex substances such as paper, curved surfaces and dark objects can be challenging. Chemical imaging of fingerprints allows unwanted background to be effectively minimized and thus shows increased contrast between the fingerprint and the substrate. FIG. 3 shows the result of a preliminary study of two-month old latent fingerprints treated with ninhydrin (amino acid) and visualized using hyperspectral imaging according the principles disclosed herein versus the results from conventional testing. As shown in FIG. 3, hyperspectral imaging presents a far superior image of the fingerprint.

Figure 4:
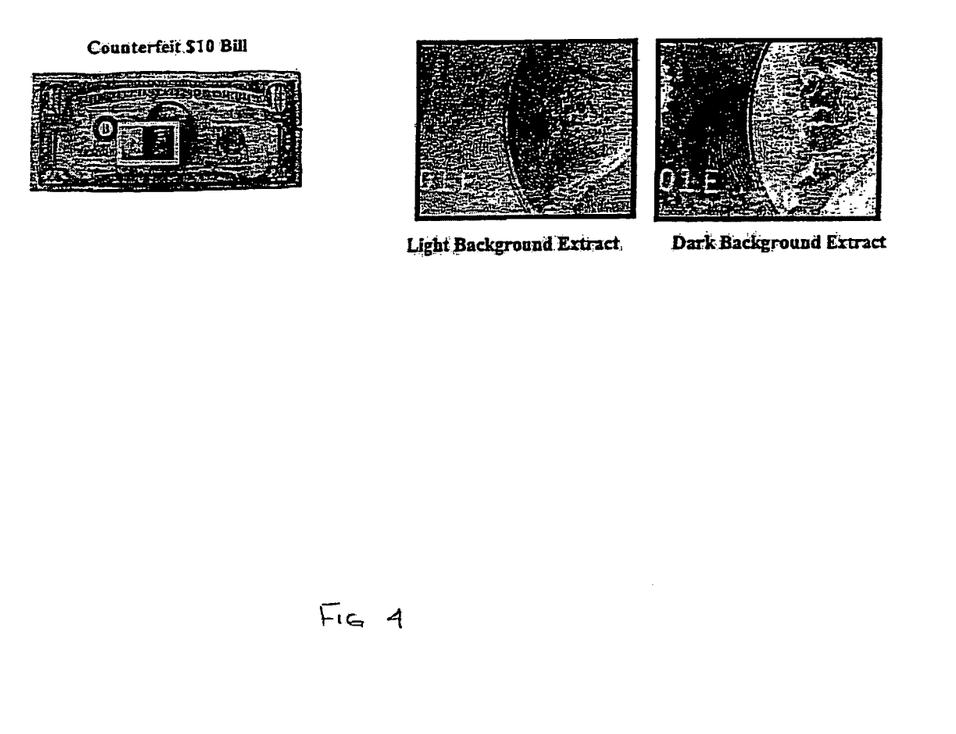
FIG. 4 shows an image of a latent fingerprint obtained according to a method disclosed herein.

FIG. 4 shows an image of a latent fingerprint obtained according to a method disclosed herein. The latent fingerprint shown in FIG. 4 was not previously detectable with the existing technology. As seen in FIG. 4, a fingerprint image can be extracted from light and dark backgrounds alike.

Figure 5A:
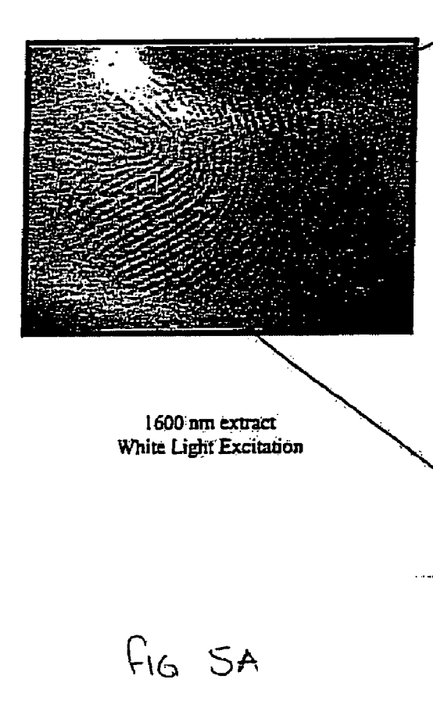
FIG. 5 shows near infrared fingerprint analysis implemented according to the principles disclosed herein.
Figure 5B:
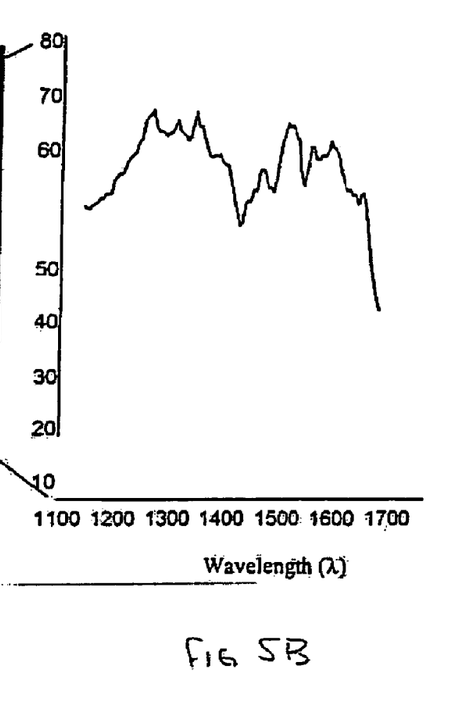

FIG. 5 shows near infrared fingerprint analysis implemented according to the principles disclosed herein. Specifically, FIG. 5 shows successful application of near infrared chemical imaging on black plastic. The hyperspectral device according to the disclosed principles can be used for macroscopic images (FIG. 5A) of the fingerprint as well as the wavelength-specific images of a segment of the fingerprint (FIG. 5B).

Figure 6:
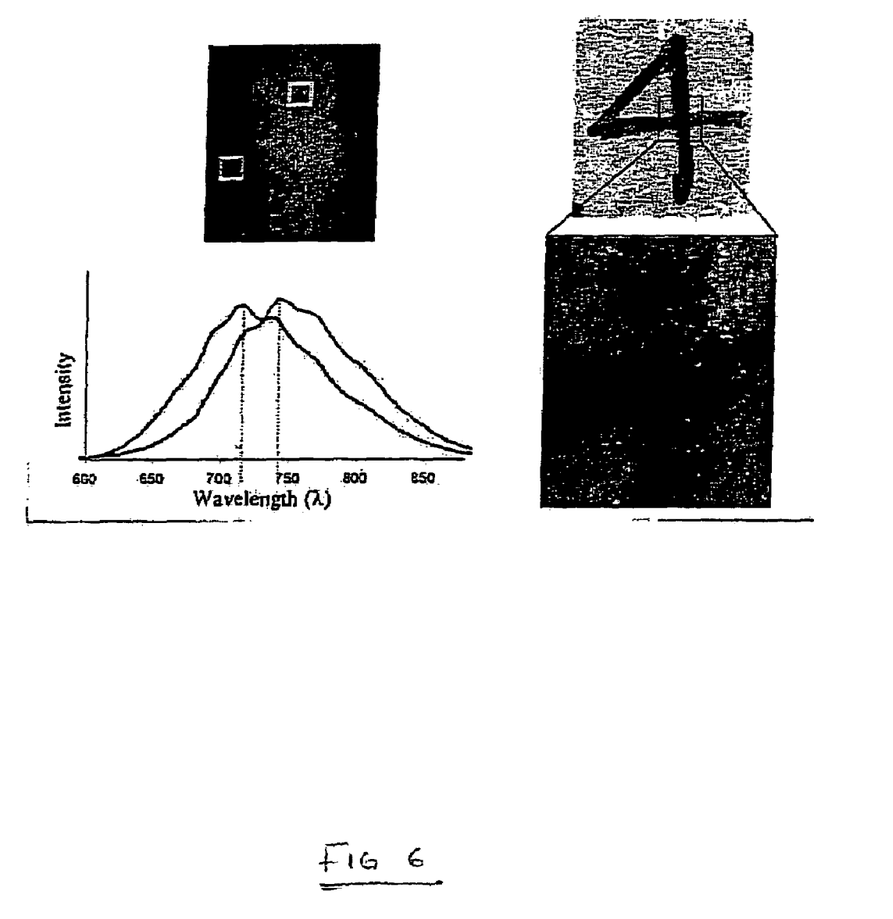
FIG. 6 shows preliminary results of fluorescence chemical imaging applied to ink discrimination in a blind study sample.

Extensive work has gone into validating the application of NIR, Raman and Fluorescence chemical imaging using this system for forensic analysis. Conventional ink visualization and comparison methods routinely employ a simple instrument configuration consisting of an excitation light source and a variety of barrier filters. Hyperspectral imaging expands on this analysis by recording an image and a fully resolved spectrum unique to the material for each pixel location in the image. This enables multiple statistical strategies to be employed to accentuate very slight color and fluorescence differences between similar inks. FIG. 6 shows the preliminary results of fluorescence chemical imaging applied to ink discrimination in blind study samples supplied by the Australian Federal Police.

Figure 7:
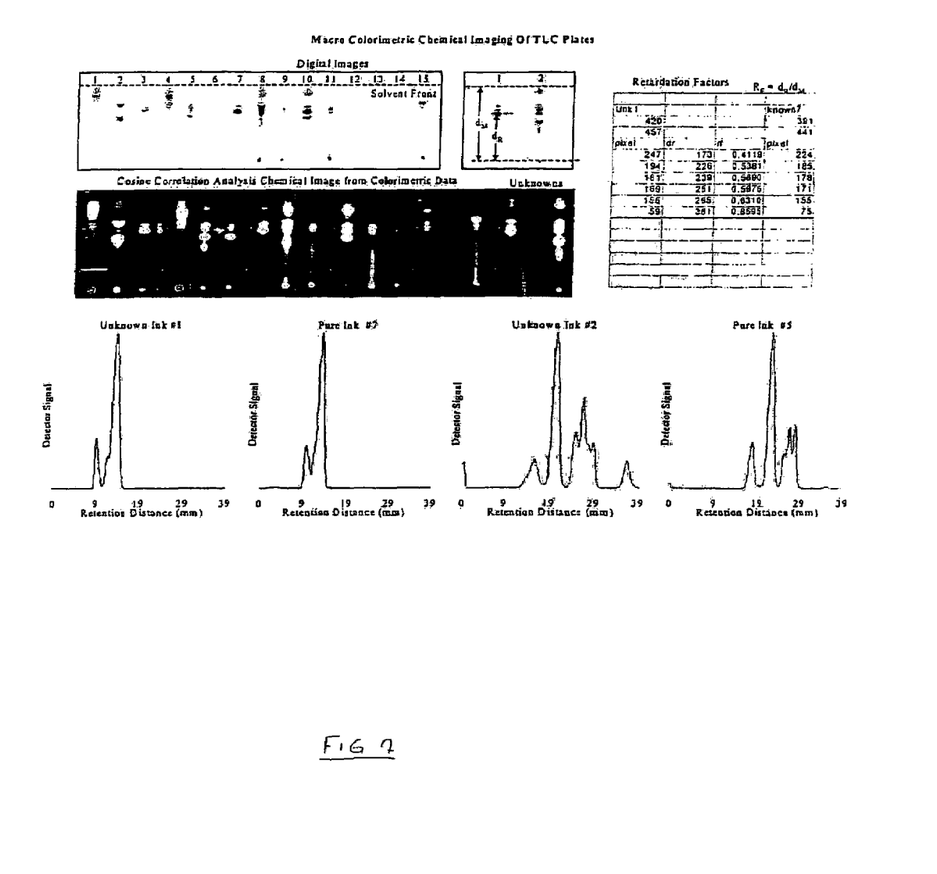
FIG. 7 shows TLC characterization according to the principles disclosed herein.

The main method in characterization of ink is thin layer chromatography. Characterization of TLC plates using colorimetric and fluorescence chemical imaging was employed for this evaluation using a microscope based platform. The value of TLC lies in its ability to spatially separate the various components of a complex matrix into a discernible pattern of bands or spots (called the band pattern). The band pattern of unknown can be compared with the band pattern of known exemplars to identify the unknown. In a similar way, TLC also routinely used to confirm the identity of dyes, explosives and drugs in the forensic laboratory. Results of a typical TLC analysis of inks are shown in FIG. 7. The top two photos show two portions of the developed TLC plate. The left picture is the TLC separation (in the vertical direction) of a set of standard ink samples and the picture on the right shows a separation, under identical conditions, of two unknown ink samples. Typically, the comparison of the TLC band patterns between knows and unknowns is done by measurement of the reflectance or optical opacity of the deposited material. The success of identifications made by these techniques is determined by the contrast between the spot and the TLC plate. Often this is hampered by the fact that many compounds separated by TLC are weakly colored. This contrast can be improved dramatically by the use of hyperspectral imaging techniques. The second set of pictures show the same TLC plates after a chemometric transform, cosine correlation, was applied to the chemical imaging data set. Cosine correlation uses the spectral differences, not just the reflectance or optical opacity of the TLC plate to provide this increased contrast. Identification of unknowns is facilitated by extracting the intensity information in the transformed data into a two-dimensional plot of intensity versus distance from where the sample was first applied. Examples of these plots and of how they can be used are shown at the bottom of FIG. 7. The data from chemical imaging analysis of ink TLC plates can also be used to calculate a quantitative measure of the separation of a mixture, the retention factor (RF). This measurement is a comparison of the movement of a separated band relative to the movement of the developing solvent and is important as it allows the comparison of TLC plates taken under different conditions. The table in the upper right corner of FIG. 7 gives the results of $R_F$ calculations used in the identification of Unknown Ink No. 1.

Figure 8:
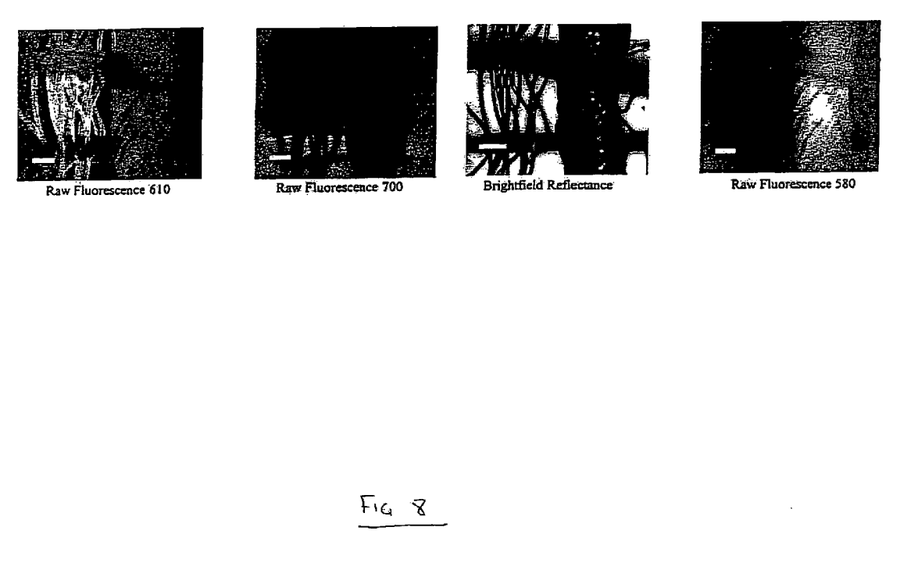
FIG. 8 shows the results of examination of fabric samples according to principles disclosed herein.

FIG. 8 shows the results of examination of a sample of clothing material without chemical preparation that is characteristic of such an extended wavelength approach. The clothing material is a weave consisting of four different types of thread (two horizontal and two vertical treads.) The visible light image of this cloth as viewed under a microscope (identified as brightfield images in FIG. 8) shows the fibers on the right and left hand sides as objects having different textures but similar opacity. The density of the weave making up a fabric is useful but not a unique characteristic of cloth. The constituent fibers can be chemically distinguished without any chemical treatment by viewing the intrinsic fluorescence from these fibers. Here, instead of detecting the visible light the sample is irradiated with UV radiation and examined with a VIS/NIR electronically tunable filter and detector. Direct spectral images without any imaging processing (referred to as "raw" in FIG. 8) are labeled by the wavelength in FIG. 8. The top horizontal threads in this weave do not seem to fluoresce while the bottom horizontal threads appear to fluoresces at 700. The fluorescence intensity of the fibers in the left image observed at 610 nm differs significant from the fluorescence intensity of the fibers on the right seen at 580 nm while little difference is found at 700 nm. These differences are from a different chemical composition of the fibers and allow this particular cloth to be distinguished by this characteristic fluorescence emission. The top horizontal weaves do not seem to fluoresce and the bottom horizontal weaves fluoresces at about 700 (in the image). Performing a multivariate analysis of the spectral images using principle component analysis can further identify all the distinct fluorescent fibers in these fluorescent images and pinpoint their locations relative to the visual image. Image fusion can be used to overlap and correlate all the images for even further information.

Other advantages of the method and apparatus for hyperspectral imaging device disclosed herein include: non-destructive identification of physical evidence, image format compatible with automated fingerprint identification system ("AFIS"), testing duration under 5 minutes, broad sample types (e.g., fingerprint, inks, stains, fibers, cloth, TLC plates, etc.), little to no sample preparation requirement, and device portability.

While the principles of the disclosure have been discussed in relation with exemplary embodiments, it should be noted that the inventive principles are not limited thereto and shall include any modification, variation or extension of these embodiments.

What is claimed is:

1. A multimodal hyperspectral imaging system for widefield spectral analysis of a sample comprising:
   a first optical lens and a second optical lens configured to interchangeably receive photons from said sample and to focus said photons;
   a plurality of tunable filters positioned in a filter housing, each of said plurality of tunable filters configured to selectively receive said focused photons from either said first optical lens or from said second optical lens and to provide wavelength-selective filtered photons;
   a first optical camera and a second optical camera, each configured to selectively receive said wavelength-selective filtered photons from a predetermined one of said plurality of tunable filters and to combine said wavelength-selective filtered photons to form a hyperspectral spatially accurate wavelength-resolved image of the sample.

2. The imaging system of claim 1, wherein said photons from said sample are selected from the group consisting of photons reflected by said sample, photons refracted by said sample, luminescence, fluorescence, photons Raman scattered by said sample, photons transmitted by said sample, photons adsorbed by said sample, and photons emitted by said sample.

3. The imaging system of claim 1, further comprising an optical mirror for selectively communicating photons from either said first optical lens or said second optical lens to a predetermined one of said plurality of the optical filters.

4. The imaging system of claim 1, wherein said filter housing is adapted to optically couple each of said first or second optical lenses with a predetermined selective one or combination of said plurality of optical filters.

5. The imaging system of claim 1, wherein said first optical lens is a NIR zoom optics or a reflective optics.

6. The imaging system of claim 1, wherein said second optical lens is a UV-VIS zoom optics or a reflective optics.

7. The imaging system of claim 1, wherein at least one of said first optical lens and said second optical lens defines an optical train.

8. The imaging system of claim 1, wherein said first optical lens and said second optical lens are further configured to simultaneously receive photons from said sample.

9. The imaging system of claim 1, wherein said first optical lens and said second optical lens are configured to sequentially receive photons from the sample.

10. The imaging system of claim 1, wherein at least one of said tunable filters is selected from the group consisting of an LCTF, an AOTF, a dielectric filter, a rotary filter and a linear variable filter.

11. The imaging system of claim 1, wherein at least one of said tunable filters is selected from the group consisting of a VIS LCTF, a SW-NIR LCTF, a MW-NIR LCTF, a LW-NIR LCTF and a UV-LCTF.

12. The imaging system of claim 1, wherein said first optical camera is selected from the group consisting of a charged couple device and a focal array device.

13. The imaging system of claim 1, wherein said second optical camera is selected from the group consisting of an InGaAs camera, an InSb camera and an MCT camera.

14. The imaging system of claim 1, wherein said second optical camera is an InSb camera.

15. The imaging system of claim 1, wherein said widefield spectral analysis is collected over a wavelength range of 250-2500 nm.

16. The imaging system of claim 1, wherein said multimodal hyperspectral imaging system is an integrated imaging device.

17. The imaging system of claim 1, wherein said hyperspectral image is a spatially accurate wavelength-resolved image of said sample in a wavelength range of 250-2500 nm.

18. The imaging system of claim 1, wherein said hyperspectral image is a spatially accurate wavelength-resolved image of said sample in a wavelength range of 250-1700 nm.

19. A method for obtaining a hyperspectral image of a sample using an integrated imaging device, the method comprising:
   illuminating said sample with a plurality of photons to produce photons from said sample;
   providing a first optical lens and a second optical lens for independently collecting and focusing said photons from said sample, said first optical lens and said second optical lens thereby providing focused photons of a first wavelength and a second wavelength, respectively;
   selectively directing said focused photons having a first wavelength to one of a plurality of optical filters and said focused photons having a second wavelength to a second of said plurality of optical filters, each of said plurality of optical filters providing a set of filtered photons of a predetermined wavelength;
   selectively directing each set of filtered photons of a predetermined wavelength to either a first photon detector or a second photon detector, said first photon detector and said second photon detector independently forming a spatially accurate wavelength-resolved image of the sample from said set of filtered photons of a predetermined wavelength.

20. The method of claim 19, wherein said photons from said sample are selected from the group consisting of photons reflected by said sample, photons refracted by said sample, luminescence, fluorescence, Raman scattered photons, transmitted by said sample, photons adsorbed by said sample, and photons emitted by said sample.

21. The method of claim 19, further comprising combining said spatially accurate wavelength-resolved images of said sample from said first optical detector and said second optical detector to form a hyperspectral image of said sample.

22. The method of claim 19, wherein said step of obtaining a hyperspectral image of said sample includes combining said set of filtered photons provided by said first optical filter with said set of filtered photons provided by said second optical filter.

23. The method of claim 19, wherein said hyperspectral image is a spatially accurate wavelength-resolved image of said sample in a wavelength range of 250-2500 nm.

24. The method of claim 19, wherein said hyperspectral image is a spatially accurate wavelength-resolved image of said sample in a wavelength range of 250-1700 nm.

25. The method of claim 19, wherein said step of selectively directing said focused photons to one of a plurality of optical filters includes optically connecting one of said first and second optical lenses to one of said plurality of optical filters, wherein said optical lens and said optical filter have an overlapping operating wavelength.

26. The method of claim 19, wherein said step of selectively directing each set of filtered photons of a predetermined wavelength to a first photon detector or a second photon detector includes optically connecting one of said plurality of optical filters to one of said photon detectors, wherein said optical filter and said photon detector have an overlapping operating wavelength.

27. The method of claim 19, wherein said first optical lens is a NIR zoom optics.

28. The method of claim 19, wherein said second optical lens is a UV-VIS zoom optics.

29. The method of claim 19, wherein at least one of said first optical lens and said second optical lens defines an optical train.

30. The method of claim 19, wherein at least one of said plurality of filters is a liquid crystal tunable filer.

31. The method of claim 19, wherein said first optical lens and said second optical lens are configured to simultaneously receive photons from said sample.

32. The method of claim 19, wherein said step of illuminating said sample includes illuminating said sample with photons having wavelengths in the range of 250-2500 nm.

33. The method of claim 19, wherein said step of illuminating said sample includes illuminating said sample with photons having wavelengths in the range of 250-1700 nm.

34. The method of claim 19, wherein said first photon detector is a silicon CCD.

35. The method of claim 19, wherein said second photon detector is an InGaAs camera.

36. The method of claim 19, wherein said second photon detector is an InSb camera.

37. The method of claim 19, wherein said step of selectively directing said focused photons to a plurality of optical filters includes using a mirror to selectively direct said focused photons from said first optical lens to at least one of said plurality of optical filters.

38. The method of claim 19, wherein said step of selectively directing said filtered photons to said first photon detector includes using a mirror to selectively direct said filtered photons from said first optical filter to said first photon detector.

39. A system for collecting a hyperspectral image of a sample comprising:
 a plurality of optical lenses for receiving photons from said sample and forming focused photons;
 a filter housing for accommodating a plurality of tunable filters, each of said tunable filters being adapted to receive focused photons from at least one of said plurality of optical lenses to form a filtered spectrum of said sample;
 a first optical camera and a second optical camera for receiving the filtered photons from the plurality of tunable filters and forming therefrom a hyperspectral spectrum of the sample;
 a controller optically connecting at least one of said plurality of optical lenses with at least one of said plurality of tunable filters.

40. The system of claim 39, wherein said photons from said sample are selected from the group consisting of photons reflected by said sample, photons refracted by said sample, luminescence, fluorescence, Raman scattered photons, photons transmitted by said sample, photons adsorbed by said sample, and photons emitted by said sample.

41. The system of claim 39, wherein said controller optically connects said at least one of said plurality of optical lenses with said at least one of said plurality of tunable filters through a mirror.

42. The system of claim 39, wherein said controller also optically connects said at least one of said plurality of tunable filters with at least one of said first optical camera and said second optical camera.

43. The system of claim 39, further comprising at least one illumination source adapted to illuminate said sample with photons having wavelengths in the range of 250-2500 nm.

44. The system of claim 39, wherein said controller matches one of said plurality of optical lenses with one or more of said plurality of tunable filters.

45. The system of claim 43, wherein said controller defines the wavelength of photons emitted by said illumination source.

46. The system of claim 39, wherein each of said plurality of optical lenses is independently selected from the group consisting of an NIR lens, a UV-VIS lens and a zoom lens.

47. The system of claim 39, wherein at least one of said plurality of optical lenses defines an optical train.

48. The system of claim 39, wherein said plurality of tunable filters includes at least one LCTF.

49. The system of claim 39, wherein each of said plurality of tunable filters is independently selected from the group consisting of a VIS LCTF, a SW-NIR LCTF, a MW-NIR LCTF, a LW-NIR LCTF and a UV-LCTF.

50. The system of claim 39, wherein said hyperspectral image is a spatially accurate wavelength-resolved image of said sample in the wavelength range of 250-2500 nm.

51. The system of claim 39, wherein said system is an integrated device.

52. The system of claim 39, wherein said controller optically connects one of said plurality of optical lenses with one of said plurality of optical tunable filters in order to match the operating wavelength of a predetermined one of said plurality of optical lenses with a predetermined one of said plurality of tunable filters.

53. An automated system for collecting a hyperspectral image of a sample, said automated system including a processor programmed to:
 (a) illuminate said sample using an illumination source having a first selected wavelength;
 (b) selectively direct one of a plurality of optical lenses to collect photons from said sample and focus said collected photons; wherein said one of said plurality of optical lenses is adapted to conform to said first selected wavelength;
 (c) direct said focused collected photons from said one of said plurality of optical lenses to an optical filter selected from a plurality of optical filters, wherein said selected optical filter is adapted to conform to said first selected wavelength and to receive said focused collected photons and to provide filtered photons;
 (d) optically transmit said filtered photons from said selected optical filter to one of a plurality of optical cameras to form an image of said sample at said first selected wavelength;
 (e) repeat steps (a)-(d) for a second selected wavelength to obtain a second image of said sample at said second selected wavelength; and
 (f) combine said first image of said sample with said second image of said sample to form a hyperspectral image of said sample.

54. The system of claim 53, wherein said photons from said sample are selected from the group consisting of photons reflected by said sample, photons refracted by said sample, luminescence, fluorescence, Raman scattered photons, photons transmitted by said sample, photons adsorbed by said sample, and photons emitted by said sample.

55. The system of claim 53, wherein said hyperspectral image is a spatially accurate wavelength-resolved image of said sample in the wavelength range of 250-2500 nm.

56. The system of claim 53, wherein said first selected wavelength is in the range of 250-700 nm.

57. The system of claim 53, wherein said second selected wavelength is in the range of 700-2100 nm.

58. The system of claim 53, wherein said first selected optical lens is a NIR lens.

59. The system of claim 53, wherein said second selected optical lens is a UV-VIS lens.

60. The system of claim 53, wherein said selected optical filter is selected from the group consisting of a VIS LCTF, a SW-NIR LCTF, a MW-NIR LCTF, a LW-NIR LCTF and a UV-LCTF.

61. The system of claim 53, wherein said optical camera is selected from the group consisting of a CCD and an InGaAs camera.

62. The system of claim 53, wherein said selected optical filter is an LCTF filter.

63. The system of claim 53, wherein the range of said first selected wavelength and the range of said second selected wavelength overlap.

64. The system of claim 53, wherein the range of said first selected wavelength and the range of said second selected wavelength do not overlap.

65. The system of claim 53, wherein said processor is further programmed to electromagnetically record said hyperspectral image of said sample.

66. The system of claim 53, wherein said selected optical filter is a rejection filter.

* * * * *